(12) United States Patent
Dickmann et al.

(10) Patent No.: US 11,517,282 B2
(45) Date of Patent: Dec. 6, 2022

(54) METHOD FOR PROVIDING COLLISION INFORMATION AND MEDICAL IMAGING DEVICE

(71) Applicant: Siemens Healthcare GmbH, Erlangen (DE)

(72) Inventors: Christoph Dickmann, Nuremberg (DE); Christian Hofmann, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 234 days.

(21) Appl. No.: 16/904,900

(22) Filed: Jun. 18, 2020

(65) Prior Publication Data
US 2020/0405256 A1 Dec. 31, 2020

(30) Foreign Application Priority Data

Jun. 28, 2019 (DE) .......................... 102019209543.7

(51) Int. Cl.
*A61B 6/00* (2006.01)
*A61B 6/10* (2006.01)
*A61B 6/03* (2006.01)
*A61B 6/04* (2006.01)

(52) U.S. Cl.
CPC .............. *A61B 6/547* (2013.01); *A61B 6/102* (2013.01); *A61B 6/4405* (2013.01); *A61B 6/461* (2013.01); *A61B 6/032* (2013.01); *A61B 6/04* (2013.01); *A61B 6/4441* (2013.01)

(58) Field of Classification Search
CPC ................................ A61B 6/102; A61B 6/547
See application file for complete search history.

(56) References Cited

U.S. PATENT DOCUMENTS

| | | |
|---|---|---|
| 2002/0118280 A1 | 8/2002 | Medlar et al. |
| 2016/0174914 A1 | 6/2016 | Lerch et al. |
| 2016/0302871 A1* | 10/2016 | Gregerson ........... A61B 5/0036 |
| 2017/0086758 A1 | 3/2017 | McCarthy et al. |

FOREIGN PATENT DOCUMENTS

| | | |
|---|---|---|
| DE | 10109219 A1 | 9/2002 |
| DE | 102014226467 A1 | 6/2016 |

OTHER PUBLICATIONS

German Office Action for German Application No. 10 2019 209 543.7 dated Jul. 4, 2019.

* cited by examiner

*Primary Examiner* — Dani Fox
(74) *Attorney, Agent, or Firm* — Harness, Dickey & Pierce, P.L.C.

(57) ABSTRACT

A method is for providing collision information. In an embodiment, the method includes acquiring first position data relating to an outer contour of an object, via at least one measuring device arranged on a gantry of a medical imaging device; receiving second position data relating to an inner contour of an opening of the gantry and/or an outer contour of the gantry; receiving movement data relating to relative movement between the gantry and the object; calculating the collision information relating to a collision of the object and the gantry, based on the first position data, the second position data and the movement data; and providing the collision information.

27 Claims, 3 Drawing Sheets

METHOD FOR PROVIDING COLLISION INFORMATION AND MEDICAL IMAGING DEVICE

PRIORITY STATEMENT

The present application hereby claims priority under 35 U.S.C. § 119 to German patent application number DE 102019209543.7 filed Jun. 28, 2019, the entire contents of which are hereby incorporated herein by reference.

FIELD

Embodiments of the invention generally relate to a method for providing collision information and a medical imaging device, in particular for an imaging examination without collision.

BACKGROUND

On a movement of a gantry of a medical imaging device relative to a patient, who is positioned on a patient supporting device of the medical imaging device, it must be ensured that the movement occurs without collision. This applies, in particular, to a movable gantry, for example a sliding gantry, which can be moved on rails, or a mobile gantry with a wheel-based chassis. The wheel-based chassis can be, for example, an omnidirectional chassis.

With a sliding gantry, the alignment of the gantry relative to the patient supporting device is typically permanently predefined by the rails.

The mobile gantry with the wheel-based chassis can be oriented via a rotational movement about a vertical axis of rotation in different angles relative to the patient supporting device. The position of the vertical axis of rotation can result, for example, from an interaction of a plurality of wheels of the wheel-based chassis.

In particular in the case of interventions, an alignment is often chosen in which the gantry and a supporting plate of the patient supporting device are arranged obliquely to each other, so in one direction of movement of the gantry the full width of an opening of the gantry is not available for receiving the supporting plate and the patient positioned on the supporting plate. When the gantry is tilted, the useful height of the opening of the gantry is reduced, so there can likewise be a higher risk of collision.

There is also an increased risk of collision with particularly corpulent patients and/or owing to positioning aids and/or instruments for navigation and/or intervention, which can be connected to the patient. A patient undergoing radiotherapy, who can be positioned via positioning aids so as to be substantially higher than the supporting plate, also potentially has an increased risk of collision.

Before a scan it must therefore firstly be checked whether an object, which has a patient, a patient supporting device and optionally further partial objects, fits in the opening of the gantry. In addition, it must be ensured, in particular in the case of interventional or surgical procedures, that this also remains the case if scans have to be carried out repeatedly in the same treatment session. Such an examination for the purpose of collision avoidance can be carried out, for example, as a test run with visual check in which the movement of the gantry and the object relative to each other is performed very slowly and observed by medical personnel from suitable viewpoints. Suitable viewpoints are located in particular at the end of the object facing away from the gantry and the end of the gantry facing away from the object and allow a view through the opening of the gantry along the direction of movement of the gantry and of the object relative to each other.

A test run of this kind over the entire required scanning area can be associated with increased stress for the medical personnel, because a collision of an instrument with the gantry can be dangerous for the patient. For example, a registration framework of a navigation system, screwed in the vertebral body, can break loose from the vertebral body due to a collision with the gantry and sometimes also injure the spinal cord.

A further possibility for reducing the collision risk is the use of a gantry with a large opening.

SUMMARY

At least one embodiment of the invention enables improved collision avoidance in a medical imaging examination. The claims take into account further advantageous aspects of the invention.

At least one embodiment of the invention relates to a method for providing collision information, comprising:

acquisition of first position data via at least one measuring device, which is arranged on a gantry of a medical imaging device, wherein the first position data relates to an outer contour of an object, receiving second position data, which relates to an inner contour of an opening of the gantry and/or an outer contour of the gantry, receiving movement data, which relates to a movement of the gantry and the object relative to each other, calculation of the collision information, which relates to a collision of the object and the gantry on movement of the gantry and the object relative to each other, based on the first position data, the second position data and the movement data, and providing the collision information.

At least one embodiment of the invention relates, moreover, to a medical imaging device, comprising:

a gantry, at least one measuring device for acquiring first position data, which is arranged on the gantry, wherein the first position data relates to an outer contour of an object, a position data-receiving unit for receiving second position data, which relates to an inner contour of an opening of the gantry and/or an outer contour of the gantry, a movement data-receiving unit for receiving movement data, which relates to the movement of the gantry and the object relative to each other, a calculating unit for calculating the collision information, which relates to a collision of the object and the gantry on movement of the gantry and the object relative to each other, based on the first position data, the second position data and the movement data, and a provision unit for providing the collision information.

At least one embodiment of the invention relates, moreover, to a method for providing collision information, comprising:

acquiring first position data, via at least one measuring device arranged on a gantry of a medical imaging device, the first position data relating to an outer contour of an object;

receiving second position data, relating to at least one of an inner contour of an opening of the gantry and an outer contour of the gantry;

receiving movement data, relating to a relative movement between the gantry and the object;

calculating the collision information, relating to a collision of the object and the gantry on relative movement between the gantry and the object, based on the first position data acquired, the second position data received and the movement data received; and providing the collision information.

At least one embodiment of the invention relates, moreover, to a medical imaging device, comprising:

a gantry;

at least one measuring unit, arranged on the gantry, to acquire first position data, the first position data relating to an outer contour of an object;

a position data-receiving unit to receive second position data, relating to at least one of an inner contour of an opening of the gantry and an outer contour of the gantry;

a movement data-receiving unit to receive movement data, relating to the relative movement between the gantry and the object;

a calculating unit to calculate collision information, relating to a collision of the object and the gantry on the relative movement between the gantry and the object, based on the first position data acquired, the second position data received and the movement data received; and a provision unit to provide the collision information.

At least one embodiment of the invention relates, moreover, to a medical imaging device, comprising:

a gantry; and at least one processor, arranged on the gantry, to acquire first position data, the first position data relating to an outer contour of an object, receive second position data, relating to at least one of an inner contour of an opening of the gantry and an outer contour of the gantry, receive movement data, relating to the relative movement between the gantry and the object, calculate collision information, relating to a collision of the object and the gantry on the relative movement between the gantry and the object, based on the first position data acquired, the second position data received and the movement data received, and provide the collision information.

BRIEF DESCRIPTION OF THE DRAWINGS

The invention will be explained below using example embodiments and with reference to the accompanying figures. The representation in the figures is schematic, highly simplified and not necessarily to scale.

In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for providing collision information, comprising:

acquisition of first position data via at least one measuring device, which is arranged on a gantry of a medical imaging device, wherein the first position data relates to an outer contour of an object, receiving second position data, which relates to an inner contour of an opening of the gantry and/or an outer contour of the gantry, receiving movement data, which relates to a movement of the gantry and the object relative to each other, calculation of the collision information, which relates to a collision of the object and the gantry on movement of the gantry and the object relative to each other, based on the first position data, the second position data and the movement data, and providing the collision information.

The object can be, in particular, an arrangement, for example an arrangement of a plurality of partial objects. The object can have, in particular, a patient supporting device and/or a patient, who is positioned on the patient supporting device. The object can also have an instrument for a medical treatment of the patient, for example an intervention instrument and/or a navigation instrument, and/or a positioning aid. The instrument can be connected, for example, to the patient and/or to the patient supporting device. The object can also have a cover, in particular a flexible sterile cover, which at least partially covers the patient and/or the instrument. The outer contour of an object, which, in addition to the patient and the patient supporting device, has an instrument, a positioning aid and/or a cover, is typically enlarged compared to an outer contour, which encloses only the patient and the patient supporting device.

The movement data can relate, for example, to a start position and/or a target position of the gantry and/or the object. The movement data can relate, for example, to a speed and/or a speed curve over time of a movement of the gantry and/or a movement of the object. The movement data can relate, for example, to a trajectory of the movement of the gantry and/or a trajectory of the movement of the object.

The movement data can comprise, for example pre-defined movement data, on the basis of which the movement of the gantry and/or the movement of the object is controlled. Pre-defined movement data can be provided, for example, based on an examination protocol for a medical imaging examination, which can be carried out via the computed tomography device. Alternatively or in addition, the movement data can comprise, for example, extrapolated movement data, which was calculated by way of an extrapolation, for example, based on the first position data, which was acquired via the at least one measuring device during a first movement section, for a second movement section following the first movement section. Alternatively or in addition, the movement data can be acquired via at least one movement measuring device.

The second position data can comprise, for example, pre-defined second position data, which is provided, for example, in the form of a geometric data set, which relates to the gantry. Alternatively or in addition, the second position data can be acquired via the at least one measuring device and/or via at least one measuring device for the inner contour of the opening of the gantry and/or the outer contour of the gantry.

The at least one measuring device can be selected, in particular, from the group comprising a 3D-camera, a laser sensor, an ultrasound sensor, a radar sensor and combinations thereof. The at least one measuring device can be arranged, for example, on an outer side of a casing of the gantry and/or inside the gantry, in particular behind a region of a casing of the gantry that is transparent for the respective sensor.

The at least one measuring device can be designed, in particular, for measuring a spatial region in three dimensions. In particular, based on the first position data for each point of the spatial region, a distance of the point from a reference point can be determined. The reference point can be defined, for example, relative to the at least one measuring device. The spatial region can be measured, for example, automatically or in a user-driven manner. The spatial region can be measured, for example, before a topogram image or a scan and can relate to the space, which is required, for the topogram image or for the scan.

A scan is taken to mean, in particular, an acquisition of acquisition data, for example projection data, of a region of the patient to be imaged via an acquisition unit of the gantry while the gantry is moved in a longitudinal direction of the patient relative to the patient and while a radiation source and/or a radiation detector of the acquisition unit rotates about the longitudinal direction of the patient.

The collision information can comprise, for example, information about whether the planned scan is possible without collision over the scanning area defined in the examination protocol in the chosen angle between rotational plane and direction of movement. Information of this kind can be output, for example, in the form of a yes/no response.

The collision information can comprise, in particular, an envelope of at least the section of the object, which can be positioned in the opening, and/or an envelope of a section of the object, which extends over a length of the scan defined in the examination protocol. The envelope can be, for example, a three-dimensional representation of the outer contour of the object, in particular in the form of a curved surface.

Alternatively or in addition, the collision information can comprise a maximum extension of the outer contour of the object in a direction, which is perpendicular to a direction of movement of the gantry and the object relative to each other. In particular a maximum extension of the outer contour of the object in a horizontal direction and/or a maximum extension of the outer contour of the object in a vertical direction can be calculated for this. Furthermore, for each maximum extension the collision information can comprise their respective longitudinal position along the direction of movement of the gantry and the object relative to each other. The direction of movement of the gantry and the object relative to each other can, in particular, be a direction of movement of the gantry and the object running through an isocenter of the gantry relative to each other. The direction of movement of the gantry and the object relative to each other can, in particular, be parallel to a longitudinal direction of a patient who is positioned on the patient supporting device for the medical imaging examination via the medical imaging device.

The collision information can comprise, for example, a free path length, about which the gantry can be maximally moved relative to the object before the collision of the object and the gantry takes place. When calculating the collision information, for example for each pair of points, which in each case comprises a point of the inner contour of the opening and/or the outer contour of the gantry and a point of the outer contour of the object, in each case a spacing of the two points of the pair of points along the direction of movement of the gantry and the object relative to each other can be calculated. The free path length can be determined, for example, as the smallest spacing of the spacings determined in this way. A movement of the gantry and the object relative to each other by slightly more than the free path length leads to a collision of the two points of the at least one pair of points, for which the smallest spacing was calculated. Such a free path length can also be determined for the case in which the movement of the gantry and the object relative to each other occurs along a horizontal direction of movement, which with a horizontal straight line, which lies in a rotational plane of the gantry, encloses an angle which is less than 80 degrees.

The collision information can comprise, for example, a representation of the free path length of the gantry in relation to the direction of movement of the gantry and/or the current position of the gantry. The collision information can comprise, for example, a representation of at least one point of the inner contour of the opening and/or the outer contour of the gantry and/or at least one point of the outer contour of the object at which the collision of the gantry and the object occurs if the gantry is moved by slightly more than the free path length relative to the object.

The collision information can comprise, for example, a representation of the outer contour of the object and/or a representation of points of the outer contour of the object at risk of collision. This representation can be, for example, three-dimensional and/or comprise camera images of regions at risk of collision. The collision information can comprise, for example, representations of a simulated collision event, in particular in the form of a video and/or for different solid angles. The simulated collision event can be calculated, for example, based on the first position data, the second position data and the movement data.

The collision information can comprise, for example, a recommendation to move the patient supporting device, in particular with details of at least one direction in which the patient supporting device should be moved, and/or with details of at least one calculated value, by which the patient supporting device should be moved in order to avoid a collision. The collision information can comprise, for example, a recommendation to change a tilt angle of the gantry by a calculated degree in order to avoid a collision. The collision information can comprise, for example, a recommendation to change the angle between a rotational plane of the gantry and the direction of movement in order to avoid a collision.

In particular it can be provided that, based on the collision information, an exchange of data occurs between a communications unit of the gantry and a communications unit of the patient supporting device, in particular automatically. In particular, the collision information can be transferred from the gantry to the patient supporting device. This allows an automatic alignment of the gantry and the patient supporting device relative to each other, so a scan can be performed without collision.

This allows safe and precise positioning of the patient, in particular when the patient only just fits in the opening of the gantry. Such a collision avoidance can be implemented in particular largely independently of the size of the object. Based on the collision information, potential collision points can be found in advance and changed. Laborious testing for freedom from collision with a plurality of people using a test run is not necessary therefore, so stress, time pressure and additional burdens on the part of the clinical user can be avoided.

To be able to calculate the collision information sufficiently accurately, it is in particular not necessary, in addition to the at least one measuring device, which is arranged on the gantry of the computed tomography device, to provide a further measuring device for acquiring position data, which relates to the outer contour of the object. In particular, no assembly of measuring devices in the examination space is necessary.

One embodiment provides that the object has a patient supporting device of the medical imaging device and/or that due to the movement of the gantry and the object relative to each other, at least one section of the patient supporting device is positioned in the opening of the gantry. The opening of the gantry can be, in particular, tunnel-shaped.

A further embodiment provides that the object rests relative to the floor of the examination space. The at least one measuring device, which is secured to the mobile gantry, is always available where the mobile gantry is currently located. The collision avoidance therefore functions largely independently of the space in which the mobile gantry is located, and/or largely independently of the patient supporting device with which the gantry interacts for the medical imaging examination. In particular, a collision with an object, located in the direction of movement in front of the gantry, for example an instrument table, can be avoided with the aid of the collision information.

In particular a defined start position of the gantry and the object relative to each other can be provided, starting from which the movement of the gantry and the object relative to each other is carried out, for example by a scan of the patient being carried out via the computed tomography device. In particular, the start position can be defined by a specified spacing and/or by a specified angle between the gantry and the patient supporting device. A further embodiment provides that the gantry is designed in such a way that, starting from a position, which differs from the start position, it is in particular distant, it can be reproducibly reliably moved into the start position. In particular, a spatial relative position of an isocenter of the gantry and an isocenter of the patient supporting device can be received and used for the calculation of the collision information.

A different embodiment provides that the patient supporting device is designed for positioning of the patient that is movable in a longitudinal direction of the patient and/or that the movement of the gantry and the object relative to each other is performed by the object being moved relative to a floor of the examination space. The collision avoidance described here can be used, in particular in the case of a veterinary medical computed tomography device, to avoid a collision of the gantry with a large animal, possibly sedated, to be examined.

The collision avoidance described here can be used, in particular, in both a medical imaging device having a closed annular geometry of the gantry, for example a computed tomography device, as well as in a medical imaging device having an open annular geometry of the gantry, for example a C-arm X-ray apparatus.

The at least one measuring device can be arranged, for example, on a housing of the C-arm X-ray apparatus. Before a scan via the C-arm X-ray apparatus, the spatial scanning area can be measured from a defined z spacing outside the scanning area, for example via the at least one measuring device. Based on the collision information it is possible to check, for example, whether the C-arm X-ray apparatus can be moved without collision into the scanning area to carry out a scan of the patient, and/or whether the C-arm X-ray apparatus can be rotated in the scanning area without collision about a longitudinal direction of the patient and/or along a longitudinal direction of the patient.

One embodiment provides that the gantry has a chassis and/or that the movement of the gantry and the object relative to each other is performed by the gantry being moved relative to a floor of an examination space. The chassis can be, in particular, a wheel-based chassis. The chassis can be, in particular, omnidirectional and/or self-driving. The chassis can be designed, in particular, for autonomous driving.

One embodiment provides that a user input, which relates to the outer contour of the object, is acquired via a user interface, and/or that the collision information is calculated on the basis, moreover, of the user input.

An interface, for example, between the object and the surroundings of the object, for example between a cover and the air surrounding the cover, can be calculated, in particular automatically, on the basis of the first position data. A marker, for example, which represents a point and/or a course of this interface, can be generated on the basis of the user input. By way of the user input, the user can manipulate the representation of the outer contour of the object in order, for example, to manually correct incorrectly identified outer contour fractions.

One embodiment provides that the gantry has a support frame and a tilting frame, which is mounted on the support frame to tilt about a horizontal tilt axis relative to the support frame, and/or that the at least one measuring device is mounted on the tilting frame to pivot about a horizontal pivot axis relative to the tilting frame.

One embodiment provides that a tilting movement of the tilting frame is performed about the horizontal tilt axis relative to the support frame and/or that a pivoting movement of the at least one measuring device is performed about the horizontal pivot axis relative to the tilting frame in such a way that the tilting movement of the tilting frame about the horizontal tilt axis and the pivoting movement of the at least one measuring device about the horizontal pivot axis are substantially compensated in relation to an alignment of the at least one measuring device relative to the object, in particular are compensated and/or are compensated in such a way that the alignment of the at least one measuring device relative to the object remains substantially unchanged, in particular remains unchanged.

In particular, the horizontal pivot axis can be parallel to the tilt axis. The at least one measuring device can be mounted on the tilting frame, for example via a pivot bearing for mounting to pivot about a horizontal pivot axis relative to the tilting frame. A pivot bearing of this kind can be designed, for example, as a roller bearing or as ball joint or in the form of a gimbal.

An embodiment provides that the at least one measuring device is mounted on the gantry to pivot about a vertical pivot axis relative to the gantry.

One embodiment provides that a rotational movement of the gantry is performed about a vertical axis of rotation and/or that a pivoting movement of the at least one measuring device is performed about the vertical pivot axis relative to the gantry in such a way that the rotational movement of the gantry about the vertical axis of rotation and the pivoting movement of the at least one measuring device about the vertical pivot axis are substantially compensated in relation to an alignment of the at least one measuring device relative to the object, in particular are compensated and/or are compensated in such a way that the alignment of the at least one measuring device relative to the object remains substantially unchanged, in particular remains unchanged.

In particular the vertical pivot axis can be parallel to the vertical axis of rotation. The at least one measuring device can be mounted on the gantry, in particular on the tilting frame, for example via a pivot bearing for the mounting to pivot about a vertical pivot axis relative to the gantry. A pivot bearing of this kind can be designed, for example, as a roller bearing or as a ball joint or in the form of a gimbal. The rotational movement of the gantry about the vertical axis of rotation can occur, for example, via an omnidirectional chassis.

According to one embodiment, the tilt axis and/or the vertical axis of rotation are located in a rotational plane of the gantry. The rotational plane of the gantry is perpendicular to the axis of rotation of the gantry about which the radiation detector and the radiation source rotate. The iso-center of the gantry is located in the rotational plane of the gantry and on the axis of rotation of the gantry.

A further embodiment provides that a pivoting movement of the at least one measuring device is designed to align the measuring device with a different spatial region. For example, first position data can be acquired for an expanded spatial region by the at least one measuring device being successively aligned, via a pivoting movement, with different subsections of the expanded spatial region. This can be advantageous in particular when no relevant objects are located in the subsection of the expanded spatial region with which the measuring device is originally aligned. Furthermore, via a pivoting movement of the at least one measuring device the alignment of the measuring device can follow a relevant object that moves from one subsection of the expanded spatial region to another subsection of the expanded spatial region.

One embodiment provides that the at least one measuring device is mounted to be movable relative to the opening of the gantry via a guide structure. The guide structure can have, for example, a rail. The guide structure can form, for example, a path around the opening of the gantry. The path can be, in particular, annular or C-arm-shaped. The path can be, in particular, open or closed. According to one embodiment, the path has one or more straight section(s). According to one embodiment, the at least one measuring device is arranged on the rotor of the gantry.

In particular, the at least one measuring device can be moved on the path around the opening of the gantry, in particular around the axis of rotation of the gantry. In particular the first position data can be acquired via the at least one measuring device while the at least one measuring device is moved on the path around the opening of the gantry, in particular around the axis of rotation of the gantry. In this way, first position data can be acquired from different sides of the object via the at least one measuring device. First position data of partially hidden regions of the object can be acquired more easily therefore.

Furthermore, a warning signal can be output if an object changes its position owing to non-stationary behavior in the region of the intended scan route, for example if a doctor moves across the intended scan route and/or a liquid flows onto the intended scan route. The warning signal can be output, for example, at the instant at which the object assumes a position in the intended scan route in which it would collide with the gantry with a continuation of the movement of the gantry along the scan route. In particular, the warning signal can be output before the beginning of a scan. Therefore, unnecessary exposure of the patient to radiation due to a discontinued scan can be avoided.

One embodiment provides that the collision information is output via an output unit to be visible and/or audible for a user.

The collision information can be provided, for example, by the collision information being displayed via a screen and/or being output as a sound signal via an audio system. Alternatively or in addition, the collision information can be provided, for example, by the collision information being written into a computer-readable storage medium and/or by the collision information being emitted in the form of an electromagnetic signal.

In particular, the collision information can be received and/or processed by a data processing system, in particular a collision avoidance system. The collision avoidance system can be integrated, for example, in the gantry, in particular in an autonomously moving gantry. According to a further embodiment, the collision avoidance system can comprise at least one subsystem, which is integrated in the gantry, and/or can comprise at least one subsystem, which is arranged independently of the gantry and/or outside of the gantry, for example is permanently installed relative to an examination space.

A data transfer between components of the medical imaging device can occur, for example, in each case via a suitable data transfer interface. The data transfer interface for data transfer to and/or from a component of the medical imaging device can be implemented at least partially in the form of software and/or at least partially in the form of hardware. The data transfer interface can be designed, for example, for storing data in and/or for loading data from a computer-readable storage medium, wherein one or more component(s) of the medical imaging device can access the computer-readable storage medium.

According to one embodiment, a warning signal can be generated and output on the basis of the collision information. The warning signal helps the user to react quickly and purposefully. The warning signal can be, for example, an audio signal, a visual signal or an audiovisual signal.

One embodiment provides that the movement of the gantry and the object occurs relative to each other along an, in particular, horizontal direction of movement, which with a horizontal straight line, which lies in a rotational plane of the gantry, encloses an angle which is less than 80 degrees, in particular less than 70 degrees.

One embodiment provides that the movement of the gantry and the object is performed relative to each other, wherein the first position data is acquired via the at least one measuring device during the movement of the gantry and the object relative to each other, wherein the collision information is calculated and provided during the movement of the gantry and the object relative to each other.

In particular, the first position data can be acquired continuously or periodically via the at least one measuring device. According to one embodiment, if required, acquisition of the first position data can be suppressed, in particular be programmatically or manually suppressed, and/or repeated.

According to a further embodiment, the method also comprises tracking a movement of the object, for example based on markers and/or a surface recognition. In particular, based on the first position data, a representation of the patient surface for successive instants and/or a movement of the patient surface and/or at least one marker applied thereto can be determined. This information can be represented in the form of a movement curve and/or a moving surface image and/or be displayed via a screen. The movements of the patient identified in this way can be used, for example, as a surrogate for movements of inner structures of the patient caused by breathing, in particular for a 4D-CT examination or an aspiration in a particular breathing phase.

One embodiment provides that the movement of the gantry and the object relative to each other is adjusted as a function of the collision information, in particular automatically adjusted, or ended, in particular automatically ended.

The collision information can comprise, for example, at least one output signal at a chassis of the gantry in order to change the movement, in particular to slow it down or stop it, or to prevent the movement.

At least one embodiment of the invention relates, moreover, to a medical imaging device, comprising:

a gantry, at least one measuring device for acquiring first position data, which is arranged on the gantry, wherein the first position data relates to an outer contour of an object, a position data-receiving unit for receiving second position data, which relates to an inner contour of an opening of the gantry and/or an outer contour of the gantry, a movement data-receiving unit for receiving movement data, which relates to the movement of the gantry and the object relative to each other, a calculating unit for calculating the collision information, which relates to a collision of the object and the gantry on movement of the gantry and the object relative to each other, based on the first position data, the second position data and the movement data, and a provision unit for providing the collision information.

One embodiment provides that the medical imaging device has a user interface for acquiring a user input, wherein the calculating unit is designed for calculating the collision information, also based on the user input.

One embodiment provides that the object has a patient supporting device of the medical imaging device and/or that due to the movement of the gantry and the object relative to each other, at least one section of the patient supporting device is positioned in the opening of the gantry. In particular, the object can be positioned relative to the gantry in such a way that due to a movement of the gantry and the object relative to each other, at least one section of the patient supporting device can be positioned in an opening of the gantry.

One embodiment provides that the gantry has a chassis and/or that the movement of the gantry and the object is performed relative to each other by the gantry being moved relative to a floor of an examination space.

One embodiment provides that the gantry has a support frame and a tilting frame, which is mounted on the support frame to tilt about a horizontal tilt axis relative to the support frame and/or that the at least one measuring device is mounted on the tilting frame to pivot about a horizontal pivot axis relative to the tilting frame.

One embodiment provides that a tilting movement of the tilting frame can be performed about the horizontal tilt axis relative to the support frame and/or that a pivoting movement of the at least one measuring device can be performed about the horizontal pivot axis relative to the tilting frame in such a way that the tilting movement of the tilting frame about the horizontal tilt axis and the pivoting movement of the at least one measuring device about the horizontal pivot axis are substantially compensated in relation to an alignment of the at least one measuring device relative to the object, in particular are compensated and/or are compensated in such a way that the alignment of the at least one measuring device relative to the object remains substantially unchanged, in particular remains unchanged.

One embodiment provides that the at least one measuring device is positioned on the gantry to pivot about a vertical pivot axis relative to the gantry.

One embodiment provides that a rotational movement of the gantry can be performed about a vertical axis of rotation and/or that a pivoting movement of the at least one measuring device can be performed about the vertical pivot axis relative to the gantry in such a way that the rotational movement of the gantry about the vertical axis of rotation and the pivoting movement of the at least one measuring device about the vertical pivot axis are substantially compensated in relation to an alignment of the at least one measuring device relative to the object, in particular are compensated and/or are compensated in such a way that the alignment of the at least one measuring device relative to the object remains substantially unchanged, in particular remains unchanged.

One embodiment provides that the medical imaging device has a gantry having an annular geometry. The annular geometry can be, in particular, open or closed. In particular, the opening of the gantry can be formed by the annular geometry of the gantry.

One embodiment provides that the medical imaging device is a computed tomography device or a C-arm X-ray apparatus.

According to a further embodiment, in the region of the opening the gantry has at least one pressure sensor, for example in the form of a pressure-sensitive film. Pressure sensor data can be acquired via the pressure sensor. The pressure sensor data can be used, in addition to the first position data, the second position data and the movement data, for calculation of the collision information. Alternatively or in addition, the pressure sensor data can be evaluated independently of the calculation of the collision information in order to define an imminent collision of the object and the gantry and prevent it, for example by immediate termination of the movement.

The medical imaging device can be chosen, for example, from the imaging modalities group, which comprises an X-ray apparatus, a C-arm X-ray apparatus, a computed tomography device (CT device), a molecular imaging device (MI device), a Single Photon Emission Computed Tomography device (SPECT device), a Positron Emission Tomography (PET device), a magnetic resonance tomography device (MR device) and combinations thereof, in particular a PET-CT device and a PET-MR device. The medical imaging device can also have a combination of an imaging modality, which is chosen for example from the imaging modalities group, and an irradiation modality. The irradiation modality can have, for example, an irradiation unit for therapeutic irradiation.

According to one embodiment of the invention, the medical imaging device has an acquisition unit, which is designed for acquisition of the acquisition data. In particular, the acquisition unit can have a radiation source and a radiation detector.

One embodiment of the invention provides that the radiation source is designed for the emission and/or excitation of radiation, in particular electromagnetic radiation, and/or that the radiation detector is designed for the detection of the radiation, in particular electromagnetic radiation. The radiation can pass, for example, from the radiation source to a region to be imaged and/or after an interaction with the region to be imaged to the radiation detector.

In the interaction with the region to be imaged, the radiation is modified and thereby becomes the carrier of information relating to the region to be imaged. In the case of interaction of the radiation with the detector, this information is acquired in the form of acquisition data.

In particular in the case of a computed tomography device and in the case of a C-arm X-ray apparatus, the acquisition data can be projection data, the acquisition unit a projection data acquisition unit, the radiation source an X-ray source, the radiation detector an X-ray detector. The X-ray detector can be, in particular, a quanta-counting and/or energy-resolved X-ray detector.

The gantry of a medical imaging device typically has a support construction on which, in particular, components of the acquisition unit, in particular the radiation source and/or the radiation detector, are arranged. The support construction of the gantry typically has such a high rigidity and strength that the components of the acquisition unit can be arranged both relative to each other and also relative to a region to be imaged in a geometry sufficiently defined for the imaging.

In the case of a computed tomography device, the gantry typically has a support frame and a rotor mounted to rotate relative to the support frame, wherein the radiation source and the radiation detector are arranged on the rotor. Optionally, the gantry can have a tilting frame mounted to tilt relative to the support frame, wherein the rotor is arranged on the tilting frame.

In the case of a C-arm-X-ray apparatus, the gantry typically has a support frame and a C-arm mounted to pivot relative to the support frame, wherein the radiation source and the radiation detector are arranged on the C-arm.

In the case of a magnetic resonance tomography device, the gantry typically has a support frame on which the main magnet and a first radio frequency antenna unit are arranged, wherein the first radio frequency antenna unit is designed in the form of a body coil, which is also known to the person skilled in the art as a body coil.

Data, in particular the second position data and/or the movement data, can be received, for example, by a signal, which carries the data, being received and/or by the data being read in, in particular being read in from a computer-readable storage medium. Data, in particular the collision information, can be provided, for example, by a signal, which carries the data, being transferred and/or by the data being written into a computer-readable storage medium and/or by the data being displayed on a screen.

Within the scope of the invention, features, which are described in relation to different embodiments of the invention and/or different claims' categories (method, use, device, system, etc.), can be combined to form further embodiments of the invention. For example, a claim relating to a device, can be developed also with features, which are described or claimed in conjunction with a method, and vice versa. Functional features of a method can be implemented by appropriately designed concrete components. In addition to the embodiments of the invention explicitly described in this application, diverse further embodiments of the invention are conceivable at which the person skilled in the art can arrive without departing from the scope of the invention which is predefined by the claims.

Use of the indefinite article "a" or "an" does not preclude the relevant features from also being present several times. Use of the expression "have" does not preclude the terms linked by way of the expression "have" from being identical. For example, the medical imaging device has the medical imaging device. Use of the expression "unit" does not preclude the object to which the expression "unit" refers from being able to have a plurality of components, which are spatially separate from each other.

In the context of the present application, the expression "based on" can in particular be understood within the meaning of the expression "by using". In particular, wording, as a consequence of which a first feature is generated (alternatively: ascertains, determines, etc.) on the basis of a second feature does not preclude the first feature from being generated (alternatively: ascertained, determined, etc.) on the basis of a third feature.

Figure 1:
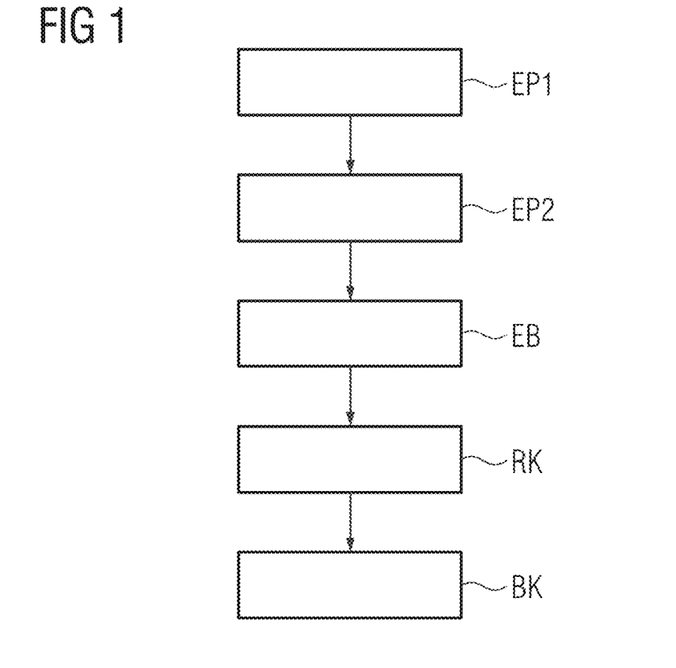
FIG. 1 shows a flowchart of an embodiment of a method for providing collision information.

FIG. 1 shows a flowchart of an embodiment of a method for providing collision information, comprising:

acquisition EP1 of first position data via at least one measuring device EP1-U, which is arranged on a gantry 20 of a medical imaging device 2, wherein the first position data relates to an outer contour of an object 1, receiving EP2 second position data, which relates to an inner contour of an opening 9 of the gantry 20 and/or an outer contour of the gantry 20, receiving EB movement data, which relates to the movement of the gantry 20 and the object 1 relative to each other, calculation RK of the collision information, which relates to a collision of the object 1 and the gantry 20 on movement of the gantry 20 and the object 1 relative to each other, based on the first position data, the second position data and the movement data, and providing BK the collision information.

Figure 2:
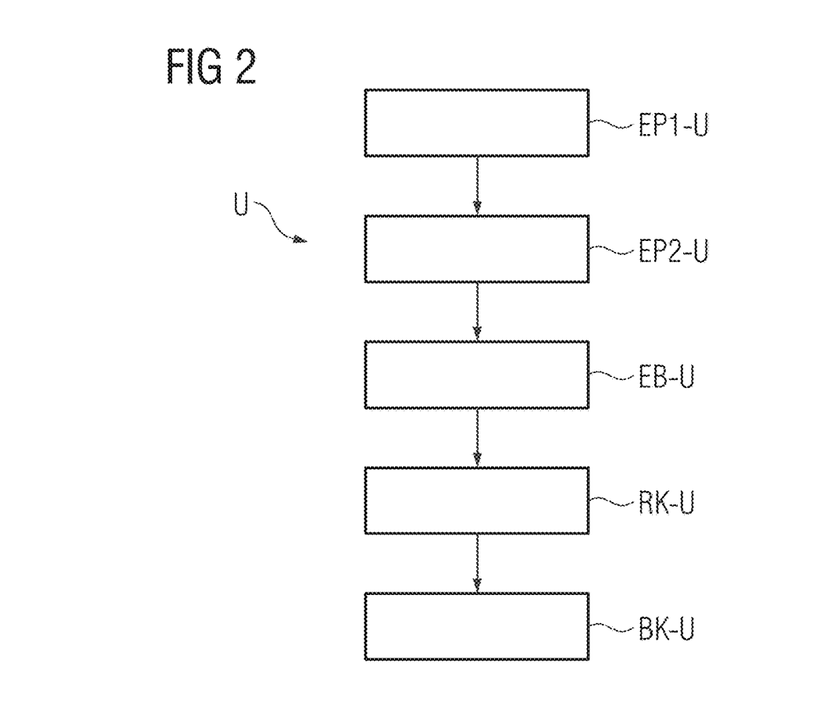
FIG. 2 shows a representation of an embodiment of a device for providing collision information.

FIG. 2 shows a representation of an embodiment of a device U for providing collision information, having:

at least one measuring device EP1-U for acquiring EP1 first position data, which is arranged on a gantry 20, wherein the first position data relates to an outer contour of an object 1, a position data-receiving unit EP2-U for receiving EP2 second position data, which relates to an inner contour of an opening 9 of the gantry 20 and/or an outer contour of the gantry 20, a movement data-receiving unit EB-U for receiving EB movement data, which relates to the movement of the gantry 20 and the object 1 relative to each other, a calculating unit RK-U for calculating RK the collision information, which relates to a collision of the object 1 and the gantry 20 on movement of the gantry 20 and the object 1 relative to each other, based on the first position data, the second position data and the movement data, and a provision unit BK-U for providing BK the collision information.

Figure 3:
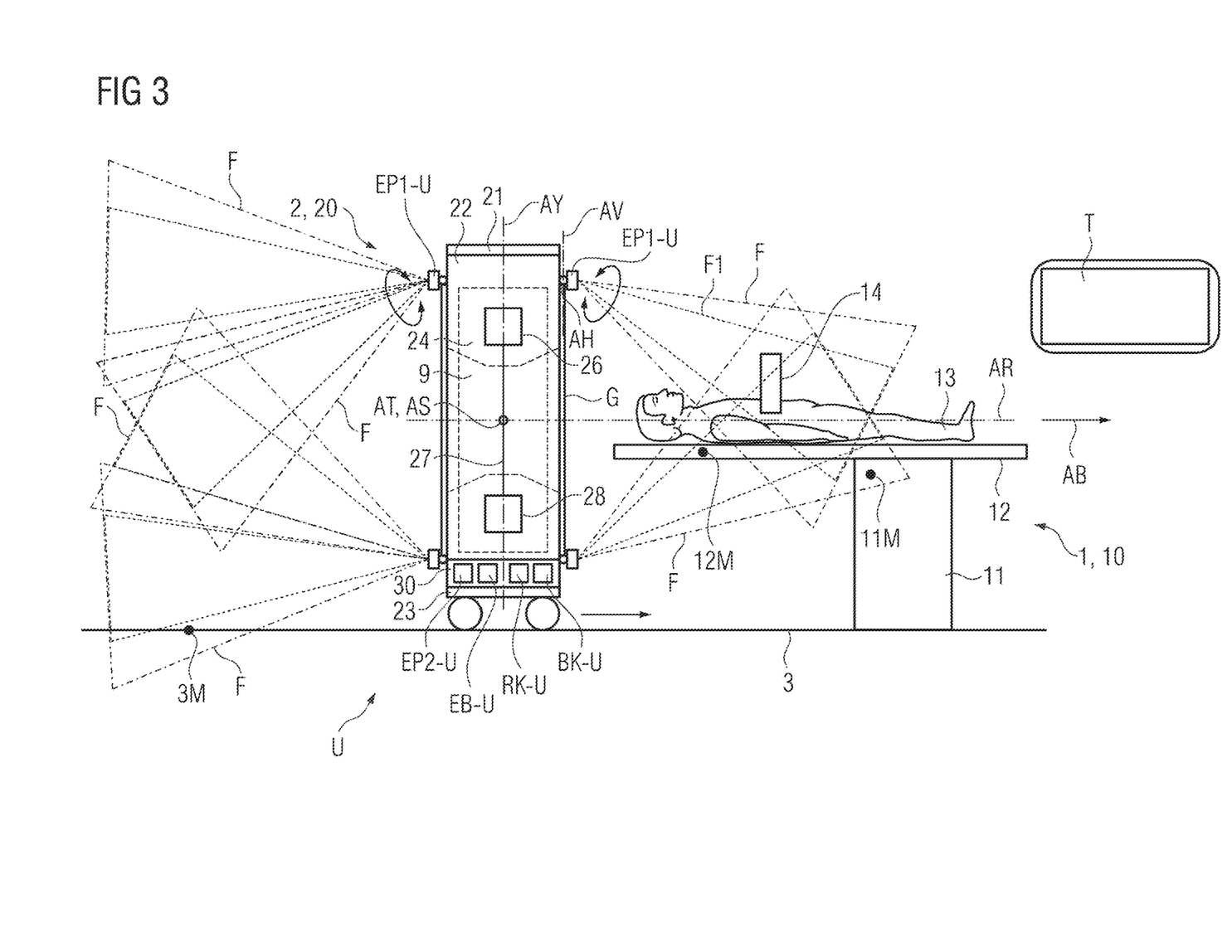
FIG. 3 shows a lateral view of an embodiment of the medical imaging device.

FIG. 3 shows a lateral view of an embodiment the medical imaging device 2, having:

a gantry 20, at least one measuring device EP1-U for acquiring EP1 first position data, which is arranged on the gantry 20, wherein the first position data relates to an outer contour of an object 1, a position data-receiving unit EP2-U for receiving EP2 second position data, which relates to an inner contour of an opening 9 of the gantry 20 and/or an outer contour of the gantry 20, a movement data-receiving unit EB-U for receiving EB movement data, which relates to the movement of the gantry 20 and the object 1 relative to each other, a calculating unit RK-U for calculating RK the collision information, which relates to a collision of the object 1 and the gantry 20 on movement of the gantry 20 and the object 1 relative to each other, based on the first position data, the second position data and the movement data, and a provision unit BK-U for providing BK the collision information.

The medical imaging device 2 of an embodiment therefore has the device U for providing collision information. The medical imaging device 2 is a computed tomography device. The object 1 has a patient supporting device 10 of the medical imaging device 2. At least one section of the patient supporting device 1 is positioned in the opening 9 of the gantry 20 by the movement of the gantry 20 and the object 1 relative to each other. The patient supporting device 10 has the supporting base 11 and the supporting plate 12 for supporting the patient 13.

The gantry 20 has a chassis 23, wherein the movement of the gantry 20 and the object 1 relative to each other is performed by the gantry 20 being moved relative to a floor 3 of an examination space. The first position data is acquired via the at least one measuring device EP1-U during the movement of the gantry 20 and the object 1 relative to each other. The collision information is calculated and provided during the movement of the gantry 20 and the object 1 relative to each other.

The medical imaging device 2 has a user interface for acquiring a user input in the form of the portable operating unit T, for example a tablet computer, wherein the collision information is calculated on the basis of the user input. The collision information is output via an output unit in the form of the portable operating unit T to be visible and/or audible for a user. The movement of the gantry 20 and the object 1 relative to each other is automatically adjusted or ended as a function of the collision information.

The medical imaging device 2 has the arithmetic unit 30 in the form of a computer, which has a processor and a computer-readable storage medium. The arithmetic unit 30 is designed for controlling the medical imaging device 2, in particular for controlling the movement of the gantry 20 based on the collision information, for example for automatically adjusting and/or for automatically ending the movement of the gantry 20 and the object 1 relative to each other.

Components of the device U for providing collision information can be designed in the form of hardware in the arithmetic unit 30 and/or in the form of software on the arithmetic unit 30. The arithmetic unit 30 has, in particular, the position data-receiving unit EP2-U, the movement data-receiving unit EB-U, the calculating unit RK-U and the provision unit BK-U.

The arithmetic unit 30 is connected to the at least one measuring device EP1-U via a connection for data transfer. In particular, the arithmetic unit 30 can receive the first position data from the at least one measuring device EP1-U. The arithmetic unit 30 is connected to the portable operating unit T via a further connection for data transfer. Connections for data transfer can be, for example, wired or wireless.

The gantry 20 has a support frame 21 and a tilting frame 22, which is mounted on the support frame 21 to tilt about a horizontal tilt axis AT relative to the support frame 21. The gantry also has the rotor 24, which is arranged on the tilting frame 22 via a pivot bearing mechanism to rotate about the axis of rotation AR relative to the tilting frame 22. The patient 13 can be introduced in the tunnel-shaped opening 9. A region of the patient 13 to be imaged can be positioned in the tunnel-shaped opening 9 in such a way that the radiation 27 can pass from the radiation source 26 to the region to be imaged and after an interaction with the region to be imaged can pass to the radiation detector 28.

The at least one measuring device EP1-U is mounted on the tilting frame 22 to pivot about a horizontal pivot axis AH relative to the tilting frame 22. A tilting movement of the tilting frame 22 can be performed about the horizontal tilt axis AT relative to the support frame 21. A pivoting movement of the at least one measuring device EP1-U can be performed about the horizontal pivot axis AH relative to the tilting frame 22 in such a way that the tilting movement of the tilting frame 22 about the horizontal tilt axis AT and the pivoting movement of the at least one measuring device EP1-U about the horizontal pivot axis AH are substantially compensated in relation to an alignment of the at least one measuring device EP1-U relative to the object 1.

The at least one measuring device EP1-U is mounted on the gantry 20 to pivot about a vertical pivot axis AV relative to the gantry 20. A rotational movement of the gantry 20 can be performed about a vertical axis of rotation AY. A pivoting movement of the at least one measuring device EP1-U can be performed about the vertical pivot axis AV relative to the gantry 20 in such a way that the rotational movement of the gantry 20 about the vertical axis of rotation AY and the pivoting movement of the at least one measuring device EP1-U about the vertical pivot axis AV are substantially compensated in relation to an alignment of the at least one measuring device EP1-U relative to the object 1. The first position data can be acquired for an expanded spatial region F by the at least one measuring device being successively aligned via the pivoting movement with different subsections F1 of the expanded spatial region.

The at least one measuring device EP1-U is mounted to move relative to the opening 9 of the gantry 20 via a guide structure G. The guide structure G has a rail and forms an annular, closed path around the opening 9 of the gantry 20. The at least one measuring device is moved on the annular closed path around the opening 9 of the gantry 20, in particular around the axis of rotation AR.

For the sake of clarity, fewer expanded spatial regions F are drawn on the side of the gantry 20 facing the patient supporting device 10 than on the side of the gantry 20 facing away from the patient supporting device 10. Using the at least one measuring device EP1-U, in particular on the two said sides of the gantry 20, first position data can be acquired, however, for spatial regions which, in relation to a direction perpendicular to the axis of rotation AR in the case of a tilted or non-tilted rotor 24, project beyond the outermost outer contour of the gantry 20, in particular comprise parts of the floor 3 and/or a ceiling of the examination space. This allows collision avoidance even immediately after a change in the direction of movement and/or scanning direction by 180 degrees, in particular while the section of the patient supporting device 13 with the patient 13 is positioned in the opening 9 of the gantry 20.

The marking 3M is on the floor. The markings 11M and 12M are on the patient supporting device 10. Position data, relating to the markings 3M, 11M and 12M, can be acquired, for example, via the at least one measuring device EP1-U. Alternatively or in addition, position data, relating to the markings 3M, 11M and 12M, can be acquired via at least one measuring device for the markings, which can be used independently of the at least one measuring device EP1-U. Based on the markings 3M, 11M and 12M, the gantry 20 and the patient supporting device 10 can be aligned relative to each other and/or be positioned in the start position. The markings 3M, 11M and 12M can be, for example, visually detectable markings and/or markings detectable via ultrasound and/or radio waves.

Alternatively or in addition to the illustrated markings, other markings can be used, which, for example, are not arranged on the floor of the examination space and/or on the patient supporting device. For example, markings can be arranged in the examination space on the ceiling of the examination space and/or on supports designed for this purpose.

Figure 4:
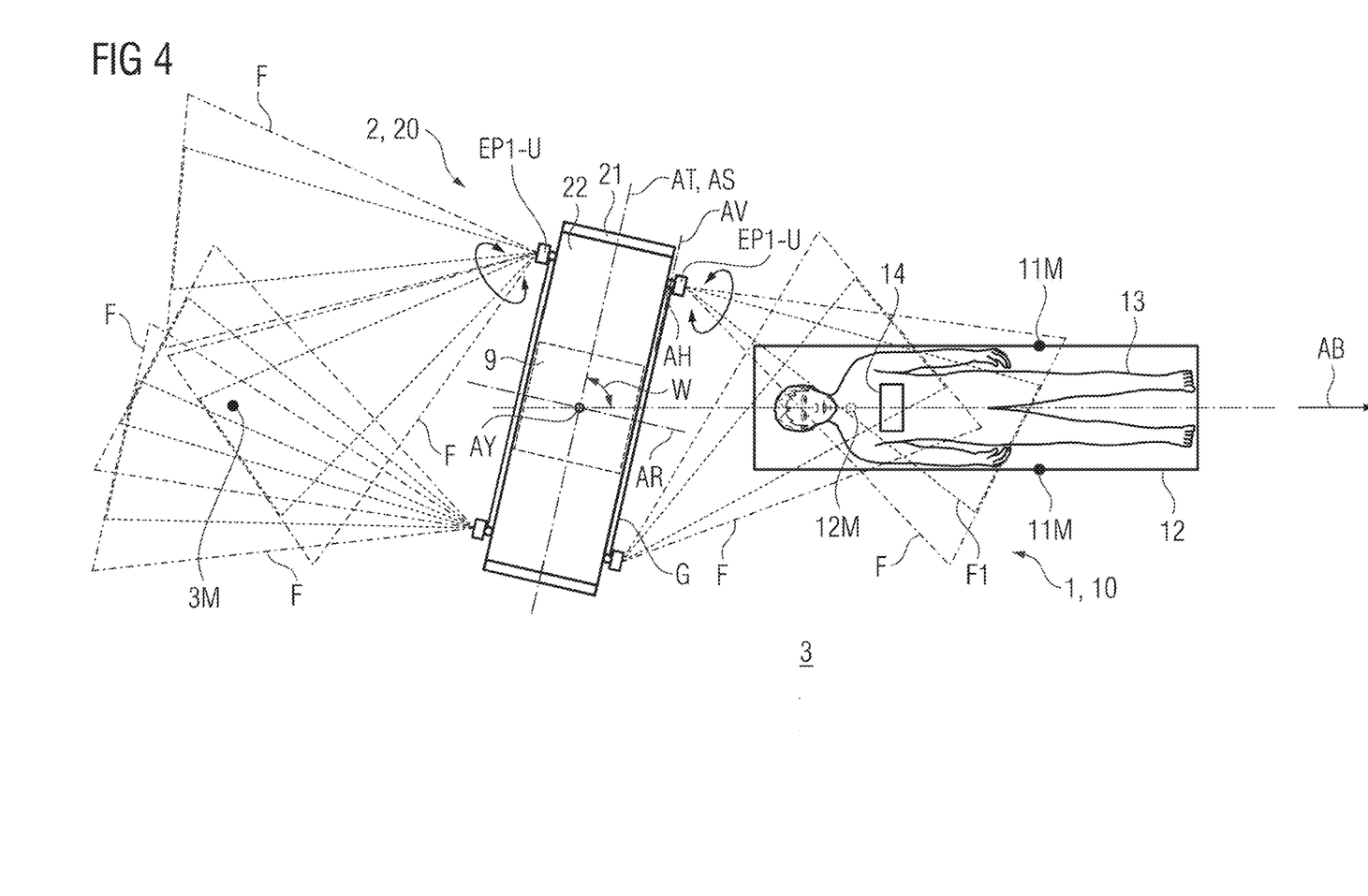
FIG. 4 shows a plan view of the medical imaging device of an embodiment in a further operating state.

FIG. 4 shows a plan view of an embodiment of the medical imaging device 2 in a further operating state, with the movement of the gantry 20 and the object 1 relative to each other occurring along a horizontal direction of movement AB, which with a horizontal straight line AS, which lies in a rotational plane of the gantry 20, encloses an angle W which is less than 80 degrees.

Although the invention has been illustrated in greater detail using the example embodiments, the invention is not limited by the disclosed examples, and a person skilled in the art can derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing collision information, the method comprising:
   acquiring first position data, via at least one measuring device arranged on a gantry of a medical imaging device, the first position data relating to an outer contour of an object;
   receiving second position data, relating to at least one of an inner contour of an opening of the gantry and an outer contour of the gantry;
   receiving movement data, relating to a relative movement between the gantry and the object;
   calculating the collision information, relating to a collision of the object and the gantry on relative movement between the gantry and the object, based on the first position data acquired, the second position data received and the movement data received, the collision information including a recommendation to change a tilt angle of the gantry by a calculated degree to avoid the collision; and
   providing the collision information.

2. The method of claim 1, wherein the object includes a patient supporting device of the medical imaging device, and the method further comprises:
   positioning at least one section of the patient supporting device in the opening of the gantry by the relative movement between the gantry and the object.

3. The method of claim 1, further comprising:
   moving the gantry relative to a floor of an examination space to perform the relative movement between the gantry and the object.

4. The method of claim 1,
wherein the gantry includes a support frame and a tilting frame, the tilting frame being mounted on the support frame to tilt about a horizontal tilt axis relative to the support frame,
wherein the at least one measuring device is mounted on the tilting frame to pivot about a horizontal pivot axis relative to the tilting frame, and
wherein the method further includes
performing a tilting movement of the tilting frame about the horizontal tilt axis relative to the support frame, and
performing a pivoting movement of the at least one measuring device about the horizontal pivot axis relative to the tilting frame such that the tilting movement of the tilting frame about the horizontal tilt axis and the pivoting movement of the at least one measuring device about the horizontal pivot axis are substantially compensated in relation to an alignment of the at least one measuring device relative to the object.

5. The method of claim 1, wherein the at least one measuring device is mounted on the gantry to pivot about a vertical pivot axis relative to the gantry, the method further comprising:
performing a rotational movement of the gantry about a vertical axis of rotation; and
performing a pivoting movement of the at least one measuring device about the vertical pivot axis relative to the gantry such that the rotational movement of the gantry about the vertical axis of rotation and the pivoting movement of the at least one measuring device about the vertical pivot axis are substantially compensated in relation to an alignment of the at least one measuring device relative to the object.

6. The method of claim 1, wherein the providing the collision information includes outputting the collision information via an output device to be at least one of visible or audible for a user.

7. The method of claim 1, wherein the relative movement between the gantry and the object occurs along a horizontal direction of movement, which with a horizontal straight line lying in a rotational plane of the gantry, encloses an angle less than 80 degrees.

8. The method of claim 1,
wherein the first position data is acquired via the at least one measuring device during the relative movement between the gantry and the object, and
wherein the collision information is calculated and provided during the relative movement between the gantry and the object.

9. The method of claim 1, wherein the relative movement between the gantry and the object is adjusted or ended as a function of the collision information.

10. The method of claim 2, further comprising:
moving the gantry relative to a floor of an examination space to perform the relative movement between the gantry and the object.

11. The method of claim 2,
wherein the gantry includes a support frame and a tilting frame, the tilting frame being mounted on the support frame to tilt about a horizontal tilt axis relative to the support frame,
wherein the at least one measuring device is mounted on the tilting frame to pivot about a horizontal pivot axis relative to the tilting frame,
wherein the method further includes
performing a tilting movement of the tilting frame about the horizontal tilt axis relative to the support frame, and
performing a pivoting movement of the at least one measuring device is performed about the horizontal pivot axis relative to the tilting frame such that the tilting movement of the tilting frame about the horizontal tilt axis and the pivoting movement of the at least one measuring device about the horizontal pivot axis are substantially compensated in relation to an alignment of the at least one measuring device relative to the object.

12. The method of claim 2, wherein the at least one measuring device is mounted on the gantry to pivot about a vertical pivot axis relative to the gantry, the method further comprising:
performing a rotational movement of the gantry about a vertical axis of rotation, and
performing a pivoting movement of the at least one measuring device about the vertical pivot axis relative to the gantry such that the rotational movement of the gantry about the vertical axis of rotation and the pivoting movement of the at least one measuring device about the vertical pivot axis are substantially compensated in relation to an alignment of the at least one measuring device relative to the object.

13. The method of claim 2, wherein the providing the collision information includes outputting the collision information via an output device to be at least one of visible or audible for a user.

14. The method of claim 2, wherein the relative movement between the gantry and the object occurs along a horizontal direction of movement, which with a horizontal straight line lying in a rotational plane of the gantry, encloses an angle less than 80 degrees.

15. A medical imaging device, comprising:
a gantry;
at least one measuring device arranged on the gantry, the at least one measuring device configured to acquire first position data, the first position data relating to an outer contour of an object; and
processing circuitry configured to cause the medical imaging device to receive the first position data,
receive second position data relating to at least one of an inner contour of an opening of the gantry or an outer contour of the gantry,
receive movement data relating to relative movement between the gantry and the object,
calculate collision information relating to a collision of the object and the gantry on the relative movement between the gantry and the object, based on the first position data acquired, the second position data received and the movement data received, the collision information including a recommendation to change a tilt angle of the gantry by a calculated degree to avoid the collision, and
provide the collision information.

16. The medical imaging device of claim 15,
wherein the object includes a patient supporting device of the medical imaging device, and
wherein at least one section of the patient supporting device is positioned in the opening of the gantry by the relative movement between the gantry and the object.

17. The medical imaging device of claim 15, wherein at least one of:
- the gantry includes a chassis; or
- the relative movement between the gantry and the object is performed by the gantry being moved relative to a floor of an examination space.

18. The medical imaging device of claim 15,
wherein the gantry includes a support frame and a tilting frame, the tilting frame being mounted on the support frame to tilt about a horizontal tilt axis relative to the support frame,
wherein the at least one measuring device is mounted on the tilting frame to pivot about a horizontal pivot axis relative to the tilting frame,
wherein the tilting frame is configured to perform a tilting movement of the tilting frame relative to the support frame about the horizontal tilt axis, and
wherein the at least one measuring device is configured to perform a pivoting movement about the horizontal pivot axis relative to the tilting frame such that the tilting movement of the tilting frame about the horizontal tilt axis and the pivoting movement of the at least one measuring device about the horizontal pivot axis are substantially compensated in relation to an alignment of the at least one measuring device relative to the object.

19. The medical imaging device of claim 15,
wherein the at least one measuring device is mounted on the gantry and configured to pivot about a vertical pivot axis relative to the gantry,
wherein the gantry is configured to perform a rotational movement about a vertical axis of rotation, and
wherein the at least one measuring device is configured to perform a pivoting movement about the vertical pivot axis relative to the gantry such that the rotational movement of the gantry about the vertical axis of rotation and the pivoting movement of the at least one measuring device about the vertical pivot axis are substantially compensated in relation to an alignment of the at least one measuring device relative to the object.

20. The medical imaging device of claim 15, wherein the medical imaging device is a computed tomography device or a C-arm X-ray apparatus.

21. The medical imaging device of claim 16, wherein at least one of:
- the gantry includes a chassis; or
- the relative movement between the gantry and the object is performed by the gantry being moved relative to a floor of an examination space.

22. The medical imaging device of claim 16,
wherein the gantry includes a support frame and a tilting frame, the tilting frame being mounted on the support frame to tilt about a horizontal tilt axis relative to the support frame,
wherein the at least one measuring device is mounted on the tilting frame to pivot about a horizontal pivot axis relative to the tilting frame,
wherein the tilting frame is configured to perform a tilting movement of the tilting frame relative to the support frame about the horizontal tilt axis, and
wherein the at least one measuring device is configured to perform a pivoting movement about the horizontal pivot axis relative to the tilting frame such that the tilting movement of the tilting frame about the horizontal tilt axis and the pivoting movement of the at least one measuring device about the horizontal pivot axis are substantially compensated in relation to an alignment of the at least one measuring device relative to the object.

23. The medical imaging device of claim 16,
wherein the at least one measuring device is mounted on the gantry and configured to pivot about a vertical pivot axis relative to the gantry,
wherein the gantry is configured to perform a rotational movement about a vertical axis of rotation, and
wherein the at least one measuring device is configured to perform a pivoting movement about the vertical pivot axis relative to the gantry such that the rotational movement of the gantry about the vertical axis of rotation and the pivoting movement of the at least one measuring device about the vertical pivot axis are substantially compensated in relation to an alignment of the at least one measuring device relative to the object.

24. A medical imaging device, comprising:
a gantry; and
at least one processor arranged on the gantry, the at least one processor configured to cause the medical imaging device to
- acquire first position data, the first position data relating to an outer contour of an object,
- receive second position data, relating to at least one of an inner contour of an opening of the gantry and an outer contour of the gantry,
- receive movement data, relating to the relative movement between the gantry and the object,
- calculate collision information, relating to a collision of the object and the gantry on the relative movement between the gantry and the object, based on the first position data acquired, the second position data received and the movement data received, the collision information including a recommendation to change a tilt angle of the gantry by a calculated degree to avoid the collision, and
- provide the collision information.

25. The medical imaging device of claim 24,
wherein the object includes a patient supporting device of the medical imaging device, and
wherein at least one section of the patient supporting device is positioned in the opening of the gantry by the relative movement between the gantry and the object.

26. The medical imaging device of claim 24, wherein at least one of:
- the gantry includes a chassis; or
- the relative movement between the gantry and the object is performed by the gantry being moved relative to a floor of an examination space.

27. The medical imaging device of claim 25, wherein at least one of:
- the gantry includes a chassis; or
- the relative movement between the gantry and the object is performed by the gantry being moved relative to a floor of an examination space.

* * * * *